(12) United States Patent
Park et al.

(10) Patent No.: US 9,044,401 B2
(45) Date of Patent: Jun. 2, 2015

(54) COMPOSITION FOR PREVENTING OR TREATING OSTEOPOROSIS, AND MANUFACTURING METHOD THEREFOR

(75) Inventors: Sang-Geun Park, Gyeonggi-do (KR);
Chang-Kyoo Lee, Gyeonggi-do (KR);
Tae-Won Lee, Gyeonggi-do (KR)

(73) Assignees: Navipharm Co., Ltd., Gyeonggi-do (KR); Dream Pharma Corporation, Seoul (KR)

( * ) Notice: Subject to any disclaimer, the term of this patent is extended or adjusted under 35 U.S.C. 154(b) by 0 days.

(21) Appl. No.: 13/698,619

(22) PCT Filed: Jun. 3, 2011

(86) PCT No.: PCT/KR2011/004067
§ 371 (c)(1),
(2), (4) Date: Dec. 21, 2012

(87) PCT Pub. No.: WO2011/155728
PCT Pub. Date: Dec. 15, 2011

(65) Prior Publication Data
US 2013/0096091 A1   Apr. 18, 2013

(30) Foreign Application Priority Data
Jun. 10, 2010 (KR) .................. 10-2010-0054921

(51) Int. Cl.
| | | |
|---|---|---|
| A61K 31/593 | (2006.01) | |
| A61K 9/20 | (2006.01) | |
| A61K 31/663 | (2006.01) | |
| A61K 45/06 | (2006.01) | |

(52) U.S. Cl.
CPC ............. *A61K 9/20* (2013.01); *A61K 31/593* (2013.01); *A61K 31/663* (2013.01); *A61K 45/06* (2013.01); *A61K 9/2095* (2013.01); *A61K 9/2077* (2013.01)

(58) Field of Classification Search
None
See application file for complete search history.

(56) References Cited

U.S. PATENT DOCUMENTS

| | | | |
|---|---|---|---|
| 6,419,955 B1 | 7/2002 | Gabel et al. ............ 424/466 |
| 2003/0195171 A1* | 10/2003 | Daifotis et al. ............ 514/89 |
| 2004/0097468 A1 | 5/2004 | Wimalawansa ........... 514/89 |
| 2005/0049225 A1 | 3/2005 | Brookler ................. 514/89 |
| 2005/0261250 A1* | 11/2005 | Daifotis et al. ............ 514/89 |
| 2009/0317460 A1* | 12/2009 | Persicaner et al. ........ 424/464 |
| 2013/0095180 A1 | 4/2013 | Lee et al. ................ 424/464 |

FOREIGN PATENT DOCUMENTS

| | | |
|---|---|---|
| EP | 2 478 909 | 7/2012 |
| JP | A 2005-531532 | 10/2005 |
| JP | A 2010-513328 | 4/2010 |
| KR | 10-2005-0110814 | 11/2005 |
| KR | 10-2012-0005228 | 1/2012 |
| KR | 10-1243747 | 3/2013 |
| KR | 10-1278572 | 4/2013 |
| WO | WO 03/086415 | 10/2003 |
| WO | WO 2005/117906 | 12/2005 |
| WO | WO 2008/026907 | 3/2008 |
| WO | WO 2008/074144 | 6/2008 |
| WO | WO 2013/058450 | 4/2013 |
| WO | WO 2013/058527 | 4/2013 |

OTHER PUBLICATIONS

Venables et al., "Powder Mixing", 2001, Drug Development and Industrial Pharmacy, vol. 27, No. 7, pp. 599-612.*
BASF, "Dry Vitamin D3 100 GFP", Technical Information, May 2005, pp. 1-2.*
Letter/Written Disclosure of the Information Disclosure Statement for the above-referenced application, mailed on Feb. 15, 2013, 2 pages.
English Abstract of Korean Patent Publication No. 10-2005-0110814, Korean Intellectual Property Organization, 1 page.
Certified English translation of International Patent Publication No. WO 2008/026907, published Mar. 8, 2008, entitled: "Pharmaceutical compositions comprising ibandronate and vitamin D3 for the treatment of osteoporosis," 9 pages.
International Search Report, issued Feb. 28, 2012, in connection with International Patent Application No. PCT/KR2011/004067, 5 pages.
International Preliminary Report on Patentability, issued Jul. 31, 2012, in connection with International Patent Application No. PCT/KR2011/004067 [English Translation], 5 pages.
Letter/Written Disclousre of the Information Disclosure Statement for the above-referenced application, mailed on Mar. 18, 2014, 2 pages.
English Abstract of International Patent Publication No. WO 2013/058450, World Intellectual Property Organization, 1 page.
English Abstract of International Patent Publication No. WO 2013/058527, World Intellectual Property Organization, 1 page.
English Abstract of Korean Patent No. KR 10-1278572 (Korean Patent Publication No. KR 10-2013-0042433; Korean Patent Application No. KR 10-2012-0069220), World Intellectual Property Organization, 1 page.
Machine English translation of International Patent Publication No. WO 2013/058450, World Intellectual Property Organization, 9 pages.
Machine English translation of International Patent Publication No. WO 2013/058527, World Intellectual Property Organization, 9 pages.

(Continued)

*Primary Examiner* — Michael B Pallay
(74) *Attorney, Agent, or Firm* — McKenna Long & Aldridge LLP; Stephanie Seidman; Frank J. Miskiel

(57) ABSTRACT

Provided is a composition for preventing or treating osteoporosis. The composition contains an ibandronic acid, or a pharmaceutically acceptable salt thereof, or a hydrate thereof, and vitamin D. The composition has uniform medicinal effects by minimizing the differences in physical properties between ibandronic acid, or the pharmaceutically acceptable salt thereof, or the hydrate thereof, and vitamin D.

13 Claims, No Drawings

(56) References Cited

OTHER PUBLICATIONS

Machine English translation of Korean Patent No. KR 10-1278572 (Korean Patent Publication No. KR 10-2013-0042433; Korean Patent Application No. KR 10-2012-0069220), Korean Intellectual Property Office, 10 pages.

Letter/Written Disclosure of the Information Disclosure Statement for the above-referenced application, mailed on Jun. 3, 2014, 2 pages.

Translation of Office Action, issued Feb. 25, 2014, in connection with corresponding Japanese Patent Application No. 2013-514106, 3 pages.

Letter/Written Disclosure of the Information Disclosure Statement for the above-referenced application, filed on Dec. 23, 2014, 2 pages.

English Abstract of Korean Patent Publication No. KR 10-2012-0005228 (Application No. KR 10-2010-0065859), World Intellectual Property Organization, 1 page.

English Abstract of Korean Publication No. KR 10-2012-0005215 (Application No. KR 10-2010-0065841), World Intellectual Property Organization, 1 page.

Machine Translation of Korean Patent No. KR 10-1243747 (Publication No. KR 10-2012-0005215; Application No. KR 10-2010-0065841), Korean Intellectual Property Office, 11 pages.

Machine Translation of Korean Patent Publication No. KR 10-2012-0005228 (Application No. KR 10-2010-0065859), Korean Intellectual Property Office, 12 pages.

Extended European Search Report and Written Opinion, issued Jul. 7, 2014, in connection with corresponding European Patent Application No. 11792639.4, 7 pages.

\* cited by examiner

COMPOSITION FOR PREVENTING OR TREATING OSTEOPOROSIS, AND MANUFACTURING METHOD THEREFOR

RELATED APPLICATIONS

This application is the National Stage of International Application. No. PCT/KR2011/004067, filed 3 Jun. 2011, which claims benefit of priority to KR-10-2010-0054921, filed 10 Jun. 2010, the specification of which is incorporated by reference herein.

TECHNICAL FIELD

The present invention relates to a composition for prevention or treatment of osteoporosis and a method for preparing the same.

BACKGROUND ART

In the body, bones have important functions. Particularly, bones provide a frame to keep the body supported and act as a reserve of minerals important to the body, most notably calcium and so play an important role in regulating the calcium balance of bloodstream. To do so, the bone maintains homeostasis through bone resorption and remodeling. Accordingly, the bone is in a dynamic state, exhibiting a metabolic balance between bone resorption and bone formation.

Osteoporosis is a bone disease that leads to an increased risk of fracture because the bone density is reduced and bone microarchitecture is disrupted with the enlargement of the medullary cavity. With the elongation of human longevity, there has been a significant increase in osteoporosis.

Osteoporosis is caused by various factors including heredity, menopause, hyperthyroidism, hyperparathyroidism, chronic renal failure, the administration of adrenocortical hormones, etc. The highest prevalence of osteoporosis is found in women who have had the experience of menopause. The estrogen deficiency following menopause is correlated with a significant increase in osteoclastic bone resorption relative to osteoblastic bone formation and with a reduction in the intestinal absorption of calcium, giving rise to trabecular bone loss, that is, a decrease in bone mineral density (BMD).

Acting as selective inhibitors of osteoclast-mediated bone resorption, bisphosphonate-based drugs have been used for the antiresorptive treatment for osteoporosis. Bisphosphonate-based drugs cause calcium to be introduced into bone, resulting in a reduction in calcium blood level. Thus, the use of bisphosphonate-based drugs must be followed by calcium supplement. In recent years, unit formulations comprising bisphosphonate and vitamin D necessary for calcium absorption have been developed, and are commercially available (for example, Fosamax Plus).

Ibandronic acid, known as a potent bisphosphonate drug with high calcium binding affinity, is developed in the form of either single-ingredient tablets or injections. Despite great demand therefor, a formulation in which ibandronic acid and vitamin D are combined in a single dosage form is difficult to prepare due to the differences in their physical properties.

DISCLOSURE

Technical Problem

It is an object of the present invention to provide a composition for prevention or treatment of osteoporosis.

It is another object of the present invention to provide a tablet for prevention or treatment of osteoporosis.

It is further another object of the present invention to provide a method for preparing a composition for prevention or treatment of osteoporosis.

Technical Solution

In accordance with an aspect thereof, the present invention provides a composition for prevention or treatment of osteoporosis, comprising ibandronic acid, a pharmaceutically acceptable salt thereof or hydrates thereof, and vitamin D.

In embodiment of the present invention, the composition may be a fixed unit formulation (fixed-dosage combination) including ibandronic acid, a pharmaceutically acceptable salt thereof or hydrates thereof, and vitamin D. That is, the composition may be a formulation in which ibandronic acid, the pharmaceutically acceptable salt thereof or the hydrates, and vitamin D are simultaneously administered in a single dosage form. For example, the composition may be a tablet including ibandronic acid, the pharmaceutically acceptable salt thereof or the hydrates thereof, and vitamin D.

In another embodiment of the present invention, the composition may include ibandronic acid, a pharmaceutically acceptable salt thereof or hydrates thereof in the form of granules, and vitamin D.

Given that the active ingredient ibandronic acid, the pharmaceutically acceptable salt thereof or the hydrates thereof is in the form of the granules, the differences in physical properties, such as density and particle size, between ibandronic acid, the pharmaceutically acceptable salt thereof or the hydrates thereof, and vitamin D may be reduced, thereby facilitating the preparation of unit formulations that have uniform physical properties.

When ibandronic acid, the pharmaceutically acceptable salt thereof or the hydrates thereof is not in the form of the granules, there may be the problem of poor sticking and flowability in mixing ibandronic acid, the pharmaceutically acceptable salt thereof or the hydrates thereof and vitamin D.

Ibandronic acid, the pharmaceutically acceptable salt thereof or the hydrates thereof may be formulated into the granules using a dry granulation process. Alternatively, a wet granulation process may be employed to prepare the granules including ibandronic acid, the pharmaceutically acceptable salt thereof or the hydrates thereof.

Preferably, the granules are formulated in the dry granulation process because heat treatment is not performed to the active ingredient of ibandronic acid, the pharmaceutically acceptable salt thereof or the hydrates thereof which thus may be stably maintained during the process. In addition, the dry granulation process allows process conditions to be easily kept constant, which is advantageous in that the granules which are of consistent quality can be produced with little fluctuation in their physical properties. Further, when the granules of ibandronic acid, the pharmaceutically acceptable salt or the hydrates thereof are produced in the dry granulation process, their density is not significantly different from that of vitamin D and thus the granules and the composition including the granules have uniform properties. Accordingly, the granules can be homogeneously mixed with vitamin D, which is greatly beneficial to the preparation of a unit formulation comprising ibandronic acid, the pharmaceutically acceptable salt or the hydrates thereof and vitamin D.

In another embodiment of the present invention, the density of the granules may range from 0.3 g/mL to 0.75 g/mL.

Given this density range, the granules may be homogeneously mixed with vitamin D because there is no significant difference in the density therebetween. Preferably, the granules have a density of from 0.4 g/mL to 0.7 g/mL and more preferably from 0.5 g/mL to 0.65 g/mL.

In another embodiment of the present invention, about 30 wt % or larger portion of the granules has a particle size of from 30 to 80 mesh (mesh according to the Korean Standard KSA5101-1). Under this condition, the granules are similar in particle size to vitamin D so that the granules and vitamin D can be homogeneously mixed and formulated into a unit formulations with optimal therapeutic efficiency. Preferably, about 50 wt % or larger portion of the granules ranges in particle size from 30 to 80 mesh. That is, the granules used in the composition of the present invention are uniform in particle size with a narrow size distribution, thus guaranteeing a uniform pharmaceutical effect to the composition.

The composition of the present invention may further include an additive such as an excipient, a lubricant, a disintegrant, etc.

Examples of the excipient useful in the composition of the present invention include lactose or a hydrate thereof, various starches, white sugar, mannitol, sorbitol, inorganic salts and a combination thereof. Magnesium stearate, talc, stearic acid, silicon dioxide or a mixture thereof may be useful as a lubricant in the composition of the present invention. Representative among the disintegrants useful in the present invention are crospovidone, croscarmellose sodium, sodium starch glycolate and a combination thereof.

The granules of the composition according to the present invention may further include an excipient and a lubricant. Suitable excipients include lactose, a hydrate thereof, cellulose and a combination thereof. For example, the granules may comprise a combination of lactose hydrate and microcrystalline cellulose. In addition, the lubricant may be magnesium stearate, silicon dioxide or a mixture thereof. For example, the granules may comprise a mixture of magnesium stearate and colloidal silicon dioxide.

In an alternative embodiment of the present invention, the composition may further comprise a lubricant and a disintegrant that are separate from the granules. The lubricant may be magnesium stearate, talc, stearic acid or a mixture thereof and the disintegrant may be crospovidone, croscarmellose sodium, sodium starch glycolate or a mixture thereof. For example, the composition may further including magnesium stearate and crospovidone that are separate from the granules.

In another embodiment of the present invention, the composition may contain ibandronic acid, the pharmaceutically acceptable salt thereof or the hydrates thereof in an amount of from 75 mg to 300 mg, and preferably in an amount of from 100 mg to 200 mg. For example, the composition may comprise 150 mg of ibandronic acid, the pharmaceutically acceptable salt thereof or the hydrates thereof. When used within this content range, ibandronic acid, the pharmaceutically acceptable salt thereof or the hydrates thereof may be readily formulated, together with vitamin D, into unit formulations. On the other hand, when the content of ibandronic acid, the pharmaceutically acceptable salt thereof or the hydrates thereof exceeds 300 mg, they may be difficult to formulate together with vitamin D.

Among the pharmaceutically acceptable salts useful in the composition of the present invention are ammonium salts, alkali metal salts, alkaline earth metal salts, and amino acid salts. For example, the pharmaceutically acceptable salt of ibandronic acid may be sodium ibandronate.

In a further embodiment of the present invention, the composition may include vitamin D in an amount of from 12,000 IU to 36,000 IU and preferably in an amount of from 20,000 IU to 30,000 IU. When present within the content range in the composition of the present invention, vitamin D may be homogeneously mixed with ibandronic acid, the pharmaceutically acceptable salt thereof or the hydrates thereof, which facilitates the preparation of unit formulations effective for the prevention or treatment of osteoporosis. In addition, the composition with such a content of vitamin D may suffice for as a calcium supplement for the blood and may be easily formulated into forms suitable for oral administration.

For use in the composition of the present invention, vitamin D may be in a form selected from among cholecalciferol, calcifediol, calcitriol, ergocalciferol and a mixture thereof and preferably in the form of cholecalciferol. For example, vitamin D may be in the form a BHT (butylated hydroxytoluene)-treated, concentrated cholecalciferol powder with a titer of from 90,000 IU/g to 120,000 IU/g.

The composition of the present invention may be administered via oral routes or parenteral routes (e.g., intravenous, subcutaneous, intraperitoneal, topical, etc.). The effective dosage of the composition depends on various factors, including the patient's weight, age, gender, state of health, diet, the time of administration, the route of administration, excretion rate, severity of diseases, etc. In general, it may be administered in a single dose per week or month. Its dose may vary depending on the content of the active ingredients ibandronic acid or its pharmaceutical acceptable salt or the hydrates, and vitamin D. For example, the composition may be administered once a month at a dose ranging from 0.5 mg/kg to 30 mg/kg and preferably from 2 mg/kg to 10 mg/kg.

In accordance with another aspect thereof, the present invention provides a tablet formulation for the prevention or treatment of osteoporosis, including ibandronic acid, the pharmaceutically acceptable salt or the hydrates thereof, and vitamin D.

In one embodiment of the present invention, the tablet formulation may include ibandronic acid, the pharmaceutically acceptable salt thereof or the hydrates thereof in the form of granules, and vitamin D.

The granules in the tablet formulation of the present invention may be prepared using a dry or wet granulation process, and preferably using a dry granulation process. Because the granules of ibandronic acid or the pharmaceutically acceptable salt or the hydrates thereof, are similar in density and particle size to vitamin D when produced in the dry granulation process, they may be homogeneously mixed with vitamin D, which is greatly beneficial to the preparation of unit formulations which show uniform physical properties over their entirety and contain high doses of ibandronic acid or the pharmaceutically acceptable salt or the hydrates thereof and vitamin D.

In accordance with a further aspect thereof, the present invention provides a method of preparing a composition for the prevention or treatment of osteoporosis, including forming ibandronic acid, a pharmaceutically acceptable salt thereof or hydrates thereof into granules, and formulating the granules, together with vitamin D, into a tablet.

The granules of ibandronic acid, the pharmaceutically acceptable salt or the hydrates thereof, used in the method of the present invention, are similar in density to vitamin D, and show a narrow particle size distribution. Hence, the formulations or unit formulations prepared from the granules and vitamin D exhibit constant physical properties.

The granules may be formed using a dry granulation process. That is, the granules may be prepared without using a solvent such as water or an organic solvent. Alternatively, the granules may be prepared in a wet granulation process which generally includes an aggregation step, a granule-making step, a drying step and a granule refining step.

In the present invention, the granules of ibandronic acid, the pharmaceutically acceptable salt thereof or the hydrates thereof may be formed so as to have a density of from 0.3 g/mL to 0.75 g/mL. Given this condition, the granules may be homogeneously mixed with vitamin D because there is no significant difference between the density of the granules and that of vitamin D.

Preferably, the granules may be prepared using the dry granulation process. Because no solvent such as water or organic solvent is employed, the dry granulation process can be performed without heating to high temperature. Accordingly, the granules of ibandronic acid, the pharmaceutically acceptable salt thereof or the hydrates thereof may be prepared without undergoing thermal degradation and can remain stable over the course of preparation of the composition. Having the advantage of maintaining process conditions over the wet granulation process, the dry granulation process guarantees that the granules have a uniform density and particle size. Further, using the dry granulation process, the granules of ibandronic acid, the pharmaceutically acceptable salt thereof or the hydrates thereof may be prepared to have a density of 0.5 g/mL or higher, which is similar to that of vitamin D. The particle sizes of 50 wt % or larger portion of the granules prepared using the dry granulation process are uniform and range from 30 mesh to 80 mesh (Korean Standard KSA5101-1). Hence, the granules of ibandronic acid, the pharmaceutically acceptable salt thereof or the hydrates thereof, prepared using the dry granulation process, may be homogeneously mixed with vitamin D and formulated into unit formulations, such as tablet formulations, which do not fluctuate in pharmaceutical efficacy.

For granulation, ibandronic acid, the pharmaceutically acceptable salt thereof or the hydrates thereof is mixed with an excipient and/or a lubricant. The mixture may be compressed into a compression material under a high pressure, followed by milling and refining to afford granules.

In the mixture for granulation, the excipient may be lactose, a hydrate, cellulose, or a mixture thereof. For example, the excipient available for granulation may be a mixture of lactose hydrate and crystalline cellulose. The lubricant may be selected from among magnesium stearate, silicon dioxide, and a mixture thereof. For example, the lubricant available for granulation may be a mixture of magnesium stearate and colloidal silicon dioxide.

The compression material may be obtained by compressing the mixture under a pressure of 2 MPa to 10 MPa and preferably under a pressure of 3 MPa to 9 Mpa. When the mixture is compressed under such a pressure, the granules will be imparted with the density and particles size which allow the granules to be homogeneously mixed with vitamin D.

Like this, when active ingredients are sensitive to moisture and heat, the granules are formed by compression under a certain pressure and then milling without heating is employed. Thus, the active ingredient ibandronic acid remains stable during the dry granulation process.

In the method of the present invention, the granules and vitamin D may be compressed in mixture of a lubricant and/or a disintegrant into a tablet.

For use in the formulation, the lubricant may be magnesium stearate, talc, stearic acid, or a combination thereof. The disintegrant may be selected from among crospovidone, croscarmellose sodium, sodium starch glycolate and a mixture thereof. For example, the granules and vitamin D may be formulated in mixture with magnesium stearate as the lubricant and crospovidone as the disintegrant into tablets.

The tablets prepared using the method of the present invention can be used as oral doses that have the same pharmaceutical efficacy from one tablet to another.

Advantageous Effects

The present invention provides a composition for prevention or treatment of osteoporosis, comprising ibandronic acid, a pharmaceutically acceptable salt thereof or hydrates thereof, and vitamin D.

The composition of the present invention may be prepared as a unit formulation by mixing vitamin D with granules of ibandronic acid, a pharmaceutically acceptable salt thereof or hydrates thereof. The granules can be homogeneously mixed with vitamin D because they have a density similar to that of vitamin D and are uniform in particle size. Accordingly, the unit formulations can be prepared with no significant difference in pharmaceutical efficacy from one to another.

MODE FOR INVENTION

A better understanding of the present invention may be obtained through the following examples which are set forth to illustrate, but are not to be construed as limiting the present invention.

In the following Examples, ibandronic acid was in the form of sodium ibandronate monohydrate and concentrated cholecalciferol powder used as vitamin D met the standard of the European Pharmacopoeia. Lactose hydrate was commercially available under the brand name of Supertab 14SD (DMV—Fonterra Excipient), microcrystalline cellulose under the brand name of Avicel 102 (FMC), colloidal silicon dioxide under the brand name of Aerosil200 (Deggusa), magnesium stearate available from Faci, crospovidone under the brand name of Kolidon CL (BASF), and povidone K-30 under the brand name of Kolidon K-30 (BASF).

Amounts of the materials used in the following Examples correspond to quantities per tablet and a total of 1000 tablets were produced with each manufacture.

Example 1

To a mixture of 168.75 mg of sodium ibandronate monohydrate, 52.75 mg of lactose hydrate and 25 mg of microcrystalline cellulose were added 1.5 mg of colloidal silicon dioxide and 5 mg of magnesium stearate. The resulting mixture for granulation was compressed using a roller compactor (Fruend, TF-Labo) under a pressure of 4 MPa to give a compression sheet. This compression sheet was reduced in size and refined with a 18 mesh (Korean Standard, KSA5101-1) in an oscillator (ERWEKA, AR-402) to afford dry granules.

The dry granules were mixed with 120 mg of conc. cholecalciferol powder and 25 mg of crospovidone and then with mg of magnesium stearate. The resulting mixture was compressed into a tablet using a rotary tablet machine (Jennchiang Machinery, JC-DH-23D).

Example 2

To a mixture of 168.75 mg of sodium ibandronate monohydrate, 61.75 mg of lactose hydrate and 25 mg of microcrystalline cellulose were added 1.5 mg of colloidal silicon dioxide and 5 mg of magnesium stearate. The resulting mixture for granulation was compressed using a roller compactor (Fruend, TF-Labo) under a pressure of 4 MPa to give compression sheet. This compression sheet was reduced in size and refined with a 18 mesh (Korean Standard KSA5101-1) in an oscillator (ERWEKA, AR-402) to afford dry granules.

The dry granules were mixed with 240 mg of conc. cholecalciferol powder and 35 mg of crospovidone and then with 3 mg of magnesium stearate. The resulting mixture was compressed into a tablet using a rotary tablet machine (Jenn-chiang Machinery, JC-DH-23D).

Example 3

Using a speedmixer (Kisan Machinary, KM-5), 168.75 mg of sodium ibandronate monohydrate, 61.25 mg of lactose hydrate and 25 mg of microcrystalline cellulose were mixed. To this mixture was added a solution of 8 mg of povidone K-30 in 0.08 mL of distilled water, followed by granulation for 4 min. The granulated material was passed through a 16 mesh (Korean Standard KSA5101-1) to make granules which were dried at 60° C. for 5 hours and refined with a 18 mesh (Korean Standard KSA5101-1) to afford wet granules.

The wet granules were mixed with 25 mg of crospovidone 25 mg and then with 2 mg of magnesium stearate. The resulting mixture was compressed into tablets using a rotary tablet machine (Jenn-chiang Machinery, JC-DH-23D).

Example 4

A mixture of 168.75 mg of sodium ibandronate monohydrate, 83.25 mg of lactose hydrate and 12 mg of microcrystalline cellulose was mixed with a solution of 8 mg of povidone K-30 in 0.08 mL of distilled water and subjected to aggregation, granulation, drying and granule refining processes the same as those of Example 3 to afford wet granules.

The wet granules were mixed with 240 mg of conc. cholecalciferol and 35 mg of crospovidone and then with 3 mg of magnesium stearate. This mixture was compressed into tablets using a rotary tablet machine (Jenn-chiang Machinery, JC-DH-23D).

Ingredients and contents used in the tablets of Examples 1 to 4 are summarized in Table 1, below.

TABLE 1

| Ingredients | Example 1 | | Example 2 | | Example 3 | | Example 4 | |
| --- | --- | --- | --- | --- | --- | --- | --- | --- |
| | mg | Wt % | mg | Wt % | mg | Wt % | mg | Wt % |
| sodium ibandronate monohydrate | 168.75 | 42.19 | 168.75 | 31.25 | 168.75 | 58.19 | 168.75 | 30.68 |
| Lactose hydrate | 52.75 | 13.19 | 61.75 | 11.44 | 61.25 | 21.12 | 83.25 | 15.14 |
| Microcrystalline cellulose | 25 | 6.25 | 25 | 4.63 | 25 | 8.62 | 12 | 2.18 |
| Colloidal silicon dioxide | 1.5 | 0.38 | 1.5 | 0.28 | — | — | — | — |
| Magnesium Stearate for granule | 5 | 1.25 | 5 | 0.93 | — | — | — | — |
| Povidone K-30 | — | — | — | — | 8 | 2.76 | 8 | 1.45 |
| Conc. Cholecalciferol powder | 120 | 30 | 240 | 44.44 | — | — | 240 | 43.64 |
| Crospovidone | 25 | 6.25 | 25 | 6.48 | 25 | 8.62 | 35 | 6.36 |
| Magnesium Stearate | 2 | 0.5 | 3 | 0.56 | 2 | 0.69 | 3 | 0.55 |

Experimental Example 1

Density of Granules

The volumes of 20 g of the granules prepared in each of Examples 1 to 4 were measured in a 100 mL mass cylinder. The densities thus obtained are given in Table 2, below.

TABLE 2

| | | Ex. 1 | Ex. 2 | Ex. 3 | Ex. 4 |
| --- | --- | --- | --- | --- | --- |
| Density (g/mL) | | 0.574 | 0.599 | 0.312 | 0.355 |
| Particle Size (Wt %) | Less than 30 mesh | 13.5 | 14.3 | 16.6 | 13.3 |
| | 30-80 mesh | 56.1 | 53.3 | 31.1 | 37.0 |
| | pass through 80 mesh | 30.3 | 32.4 | 52.3 | 49.7 |

As is apparent from the data of Table 2, the granules of Examples 1 to 4 exhibited a density of about 0.3 g/mL or greater, which is not significantly different from the density of conc. cholecalciferol, 0.65 g/mL. Particularly, the density of the granules of Examples 1 and 2 were 0.5 g/mL which is similar to that of conc. cholecalciferol powder. Due to the similar densities between the granules and vitamin D, they were more homogenously mixed with each other.

Experimental Example 2

Particle Size of Granules

Particle sizes of the granules prepared in Examples 1 to 4 were analyzed using a sieve shaker. After sieving 10 g of the granules, the weights of the granules which were retained on the 30 mesh sieve and the 80 mesh sieve (Korean Standard KSA5101-1) were measured, respectively. The weights of the granules which were retained on the mesh sieves and passed through the sieves were expressed as percentages of the initial weight of 10 g in Table 2.

As can be seen in Table 2, a 40 wt % or greater portion of the granules of Examples 1 to 4 had a particle size of 80 mesh or less. Particularly, the granules of Examples 1 and 2 had a particle size of 80 mesh or less in the 70 wt % or higher portion thereof, and showed a narrow particle size distribution, with a particle size ranging from 30 mesh to 80 mesh in a 50 wt % portion thereof.

Experimental Example 3

Ingredient Content of Each Tablet

During the production of tablets in Examples 1 to 4, several tablets were chosen in each of the initial, the mid and the late phases of the tableting process. Titers (%) of sodium ibandronate monohydrate and cholecalciferol in each tablet were measured by liquid chromatography (Alliance 25695 manufactured by Waters) and the results are summarized in Table 3, below. The relative standard deviation was calculated as concerns the titer measurements of the tablets obtained in the initial, the mid and the later phase of the tabletting process. The results are also given in Table 3.

TABLE 3

| Content Uniformity | Phase of tabletting process | Example 1 | Example 2 | Example 3 | Example 4 |
|---|---|---|---|---|---|
| sodium-Ibandronate monohydrate | Initial | 99.5 | 100.6 | 101.6 | 85.9 |
| | Mid | 98.7 | 98.9 | 100.9 | 98.4 |
| | Late | 101.3 | 98.6 | 97.6 | 119.4 |
| | Avg. | 99.8 | 99.4 | 100 | 101.4 |
| | RSD (%) | 1.33 | 1.09 | 2.14 | 16.91 |
| Cholecalciferol | Initial | 104.2 | 104.5 | | 123 |
| | Mid | 107.2 | 103.9 | | 114.2 |
| | Late | 102.7 | 106.2 | | 79.5 |
| | Avg. | 104.7 | 104.9 | | 105.6 |
| | RSD (%) | 2.19 | 1.14 | | 21.79 |

As can be seen in Table 3, a tableting process employing a granulation step, whether wet or dry, like in Examples 1 to 4, produced tablets without causing problems in terms of sticking and flowability. In addition, after tabletting, sodium ibandronate monohydrate and cholecalciferol were observed to have an average titer of from 99.4 to 105.6%, which falls within the standard range for final product, 90 to 110%.

Particularly, as concerns the tablets of Examples 1 and 2, all the relative standard deviations of the sodium ibandronate monohydrate and cholecalciferol in the tablets obtained in the initial, the mid and the later phase were approximately 2%. That is, the tablets of Examples 1 and 2 were almost uniform in the content of sodium ibandronate monohydrate and cholecalciferol irrespective of the phase of the tableting process. Accordingly, the granules of Examples 1 and 2 and vitamin D were homogeneously mixed with each other.

INDUSTRIAL APPLICABILITY

The present invention provides a composition for the prevention or treatment of osteoporosis, comprising ibandronic acid, a pharmaceutically acceptable salt thereof or hydrates thereof, and vitamin D.

The composition of the present invention may be prepared as a unit formulation by mixing vitamin D with granules of ibandronic acid, the pharmaceutically acceptable salt thereof or the hydrates thereof. The granules can be homogeneously mixed with vitamin D because they have a density similar to that of vitamin D and are uniform in particle size. Accordingly, the unit formulations are not different in pharmaceutical efficacy from one to another.

The invention claimed is:

1. A tablet for prevention or treatment of osteoporosis, comprising:
   ibandronic acid, a pharmaceutically acceptable salt thereof or hydrates thereof contained in granules having a density of from 0.4 g/mL to 0.7 g/mL; and
   vitamin D having a density about the same as the density of the granules,
   wherein:
   the amount of ibandronic acid, the pharmaceutically acceptable salt thereof or the hydrates thereof in the tablet is from 100 mg/tablet to 300 mg/tablet; and
   the amount of vitamin D in the tablet is from 12,000 IU/tablet to 36,000 IU/tablet.

2. The tablet of claim 1, wherein the granules are formed using a dry granulation process.

3. The tablet of claim 1, wherein a 50 wt % or larger portion of the granules has a particle size in the range of from 30 mesh to 80 mesh.

4. The tablet of claim 1, further comprising at least one additive selected from among an excipient, a lubricant and a disintegrant.

5. The tablet of claim 1, wherein the pharmaceutically acceptable salt is selected from among an ammonium salt, an alkali metal salt, an alkaline earth metal salt and an amino acid salt.

6. The tablet of claim 1, wherein the vitamin D is at least one selected from among cholecalciferol, calcifediol, calcitriol and ergocalciferol.

7. A method of preparing a tablet for prevention or treatment of osteoporosis, comprising:
   granulating ibandronic acid, a pharmaceutically acceptable salt thereof or hydrates thereof to form granules having a density from 0.4 g/mL to 0.7 g/mL; and
   adding vitamin D having a density about the same as the density of the granules to the granules to give a mixture; and
   compressing the mixture into a tablet,
   wherein the amount of ibandronic acid, the pharmaceutically acceptable salt thereof or the hydrates thereof in the tablet is from 100 mg/tablet to 300 mg/tablet; and
   the amount of vitamin D in the tablet is from 12,000 IU/tablet to 36,000 IU/tablet.

8. The method of claim 7, wherein the granulating comprises:
   adding an excipient and a lubricant to the ibandronic acid, the pharmaceutically acceptable salt thereof or the hydrates thereof to give a granulation mixture;
   compressing the granulation mixture into a compression material; and
   pulverizing the compression material into particles and refining the particles according to size.

9. The method of claim 8, wherein the granulation mixture is compressed under a pressure of from 2 MPa to 10 MPa.

10. The method of claim 7, further comprising:
    adding to the mixture at least one additive selected from among a lubricant and a disintegrant to give a mixture composition; and
    compressing the mixture composition into the tablet.

11. A tablet, comprising:
    ibandronic acid, a pharmaceutically acceptable salt thereof or hydrates contained in granules having a density of from 0.5 g/mL to 0.7 g/mL; and
    vitamin D having a density about the same as the density of the granules, wherein:
    the amount of ibandronic acid, the pharmaceutically acceptable salt thereof or the hydrates thereof in the tablet is from 100 mg/tablet to 300 mg/tablet; and
    the amount of vitamin D in the tablet is from 12,000 IU/tablet to 36,000 IU/tablet.

12. A tablet, comprising:
ibandronic acid, a pharmaceutically acceptable salt thereof or hydrates thereof and contained in granules having a density of from 0.4 g/mL to 0.7 g/mL; and
a cholecalciferol powder having a density about the same as the density of the granules, wherein:
the amount of ibandronic acid, the pharmaceutically acceptable salt thereof or the hydrates thereof in the tablet is from 100 mg/tablet to 300 mg/tablet; and
the amount of cholecalciferol in the tablet is from 12,000 IU/tablet to 36,000 IU/tablet.

13. A tablet, comprising:
sodium ibandronate monohydrate contained in granules having a density of from 0.4 g/mL to 0.7 g/mL; and
a cholecalciferol powder having a density about the same as the density of the granules,
wherein:
the amount of sodium ibandronate monohydrate in the tablet is from 100 mg/tablet to 300 mg/tablet; and
the amount of cholecalciferol in the tablet is from 12,000 IU/tablet to 36,000 IU/tablet.

\* \* \* \* \*